United States Patent [19]

Colon et al.

[11] Patent Number: 4,908,028
[45] Date of Patent: Mar. 13, 1990

[54] VALVE INCORPORATING AT LEAST ONE ROCKING FLAP WITH RESPECT TO ELASTIC PIVOTS

[76] Inventors: Jean Colon, 3 Rue des Ecoles, Saint-Jean-en Royans, France, 26190; Pierre Marion, Tour Carré Chemin de l'ancienne Eglise, Poleymieu Neuville-sur-Saône, France, 69250

[21] Appl. No.: 169,590

[22] Filed: Mar. 17, 1988

[30] Foreign Application Priority Data

Mar. 20, 1987 [FR] France .................. 87 04107

[51] Int. Cl.⁴ .............................. A61F 2/24
[52] U.S. Cl. .................... 623/2; 137/512.1; 137/527
[58] Field of Search ............ 623/2; 137/512.1, 527

[56] References Cited

U.S. PATENT DOCUMENTS

| | | | |
|---|---|---|---|
| Re. 31,040 | 9/1982 | Possis | 623/2 |
| 3,448,465 | 6/1969 | Pierce et al. | 623/2 |
| 4,159,543 | 7/1979 | Carpentier | 623/2 |
| 4,272,854 | 6/1981 | Bokros | 623/2 |
| 4,276,658 | 7/1981 | Hanson et al. | 623/2 |
| 4,451,937 | 6/1984 | Klawitter | 623/2 |
| 4,643,732 | 2/1987 | Pietsch et al. | 623/2 |

Primary Examiner—Richard J. Apley
Assistant Examiner—Stephanie L. Iantorno
Attorney, Agent, or Firm—Dowell & Dowell

[57] ABSTRACT

A valve incorporating at least one rocking flap which is fixedly mounted to at least one elongated elastic element whose ends project outwardly with respect to the flap and are fixedly secured to a ring member and wherein the elastic element acts as a torsion bar which functions to return the flap to its original position after the flap has been pivoted with respect to the ring member.

11 Claims, 2 Drawing Sheets

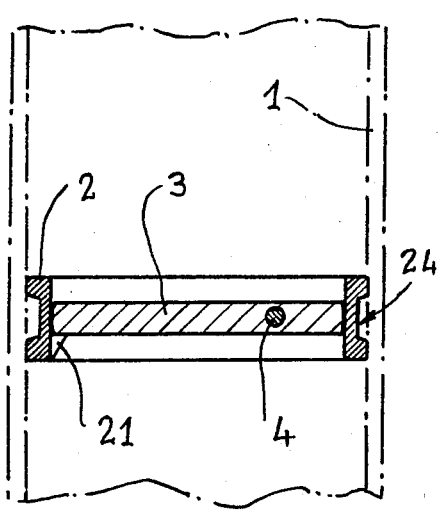
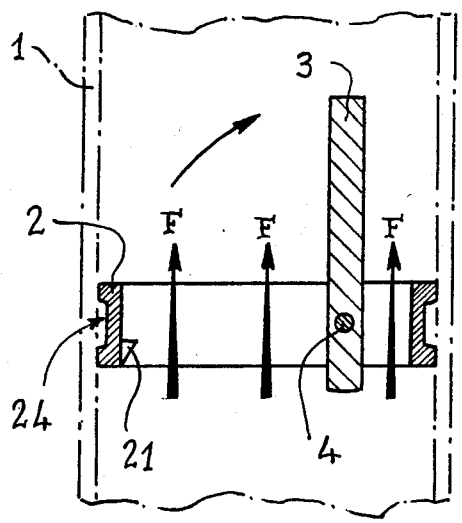
Fig. 1
Fig. 2
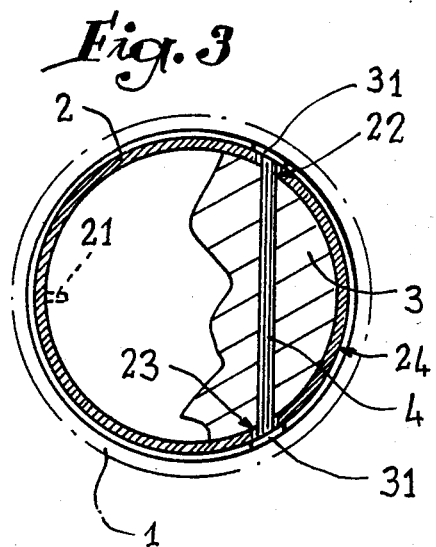
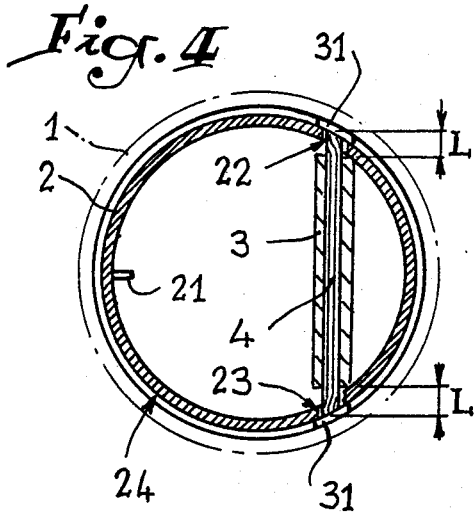
Fig. 3
Fig. 4

VALVE INCORPORATING AT LEAST ONE ROCKING FLAP WITH RESPECT TO ELASTIC PIVOTS

BACKGROUND OF THE INVENTION

The present invention relates to improvements in values with rocking flap used in passageways to constitute non-return valves, i.e. allowing the passage of a fluid only in one direction. The invention refers more particularly to valvular heart prostheses, as it is in that case that its application appears to present the greatest interest.

HISTORY OF THE RELATED ART

As is known, since the sixties, surgeons have been replacing the orifices of the heart affected by stenosis or insufficiency by mechanical or biological prostheses. So-called mechanical prostheses, i.e. with ball, disc or value, were used before so-called biological prostheses (pre-treated heterograft supported by a rigid device).

The clinical results based on numerous statistics have led to two observations:

1. The mechanical prostheses (those which do not disturb the haemodynamics and which respond to good tests of reliability assessed on models) have a satisfactory operational life of more than ten years, possibly exceeding twenty years. The percentage of premature accidents is low (rupture, precocious wear). On the contrary, the precocious or late thrombo-embolic accidents after the placing of a mechanical prosthesis are not exceptional (assessed between two and six per cent per patient and per year) especially in mitral position.

2. After a biological prosthesis has been placed, thrombo-embolic accidents are less frequent than after a mechanical prosthesis has been placed (about one to three per cent per patient/year). However, the biological prostheses are less reliable than the mechanical prostheses (on average, their life duration is less than ten years). Their dysfunction, very precocious in the child, is the consequence of valvular calcifications which provoke rigidity, stenosis and insufficiency.

Among the valve prostheses, certain use a hingeless retention device, for example the one described in AU-A-56266/69. Such a prosthesis has the drawback of requiring a metal or plastic device fixed on the ring which is generator of turbulences or possibly of catching of the figured elements of the blood and of the fibrin in the juxta-annular stasis zone of the fluid vein.

Other models are hinged flaps. Several prostheses of this type are constituted by two hinged flaps disposed like butterflies' wings, with lateral opening. The hinge is of a special type, such as that described in FR-A-2 407 709, constituted by a pivot which, engaged in an annular cavity, is scavenged by the blood and avoids stasis at that level.

FR-A-2 515 506 discloses a hinged prosthesis with two curved flaps of unequal surface of which the axes of rotation of the flaps are placed at two different levels in the ring. Due to this arrangement, the large flap, of which the axis is placed upstream of that of the small flap, opens before the latter, provoking the opening of the small one. This positioning is intended to reduce the fatal turbulences at the moment of opening of a flap.

Whatever the type of valved prosthesis (with or without hinge), blockage of the flap in open position parallel to the axis of the stream is known to be a serious accident. In order to avoid it, it is recommended to curve the flap and/or to limit the opening thereof. However, the risk of too curved a profile is to provoke an effect of stenosis. The same risk is run when reducing by stops the opening of the flap in order to avoid it reaching the position of total opening. Finally, hinged valves pose the technical problem of their introduction and positioning in a rigid ring. All the solutions proposed have their drawbacks and risks.

SUMMARY OF THE INVENTION

It is an object of the invention to improve the haemodynamic functioning and to reduce the turbulences, source of thrombosis, in mechanical prostheses with value.

BRIEF DESCRIPTION OF THE DRAWING

The invention will be more readily understood on reading the following description with reference to the accompanying drawings, in which:

FIG. 1 is a central longitudinal section through a rocking register according to the invention, in its position of closure.

FIG. 2 is a view similar to that of FIG. 1, but showing the flap open.

FIGS. 3 and 4 are transverse sections made in the plane of the pivot of the flap of FIGS. 1 and 2.

DESCRIPTION OF THE PREFERRED EMBODIMENT

Figure 5:
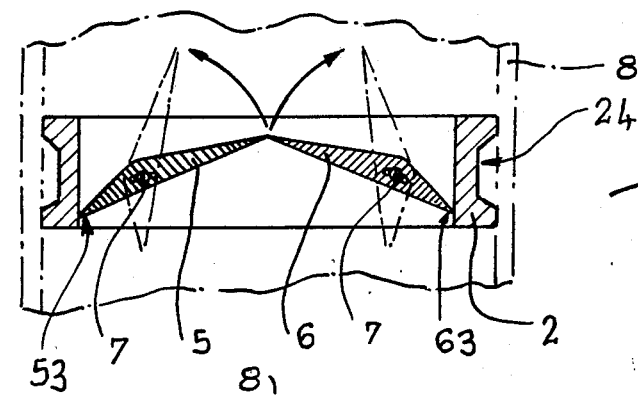
FIG. 5 illustrates a variant embodiment comprising two flaps, of which the articulation is made according to the invention.

Referring now to the drawings, the embodiments of FIGS. 1 to 4 concern more particularly, but not exclusively, an industrial application of the invention.

In a passageway 1, illustrated in broken lines, has been placed a ring 2 presenting the same profile in plan as that of the passageway 1 and in which is mounted a disc 3 of section corresponding to the inner section of the ring and rocking about a pivot 4. In a rest position, the disc 3 rests on a stop 21 of the ring 2.

As shown in FIG. 2, if a fluid flows in the passageway 1 in the direction of arrows F, the disc or butterfly 3 is displaced by the force of the current and it is oriented in the direction thereof, i.e. substantially perpendicular with respect to the passageway in question.

The problem raised is the return of the disc or butterfly 3 into its initial position when the stream of fluid ceases.

In accordance with the invention, the pivot 4 is made in the form of a rod of elastic material such as spring steel, of which that part cooperating with the disc 3 is fastened by welding, punching or otherwise to the disc in question. The pivot is eccentric with respect to the disc. Its parts project beyond the periphery thereof penetrate in two bores 22–23 of the same geomemtrical axis made in the ring 2. The ends of the pivot 4 are fixedly secured to the outside of the ring 2. In this way, a double torsion bar is formed on those parts of the pivot 4 located in the thickness of the ring 2. The bores 22 and 23 form, on the one hand, a bearing for rotation of the pivot 4 and, on the other hand, a free space in which the pivot may perform its role as a torsion bar. Of course, the diameter of the pivot 4 is determined so that the disc or flap 3 can open under the effect of the pressure generated by the passage of the fluid.

It goes without saying that the pivot 4 may be made in two parts fixedly secured on the one hand to the disc and on the other hand to the outside of the ring 2 so that there are two aligned torsion bars. It will be noted that each end part of the pivot 4 may be fastened by any means to outside the ring, for example by engaging it in the ribbed bore of a boss 31 which is secured with the periphery of the ring, the end parts of the pivot likewise being ribbed.

Figure 6:
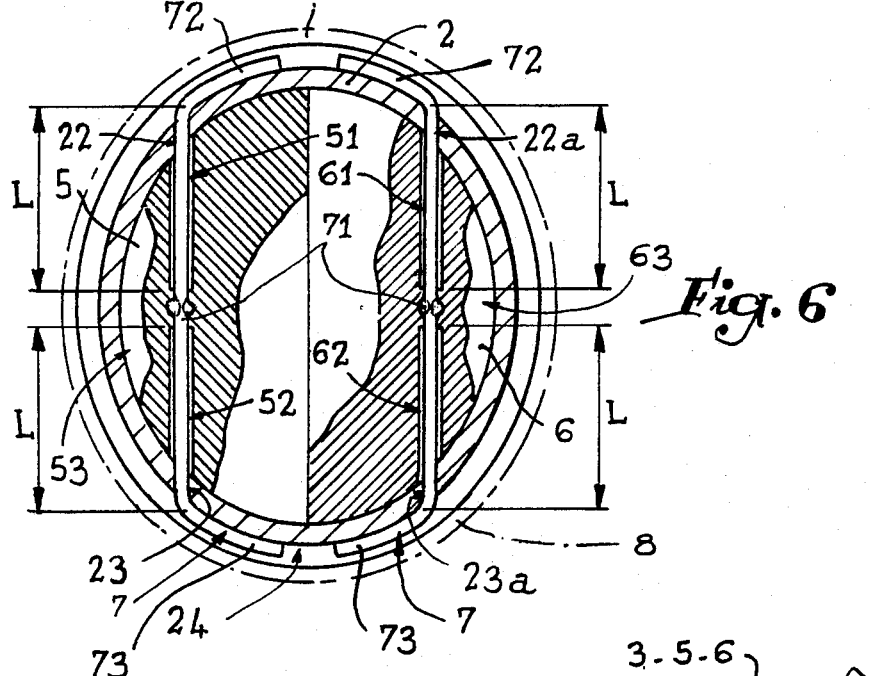
FIG. 6 is a transverse section through the plane containing the pivots of the two flaps.

In a particularly advantageous embodiment of the invention, the function of torsion bar is used in a valvular heart prosthesis illustrated very schematically in FIGS. 5 and 6.

In this application, one, two or several flaps are used. In the example schematically shown in Figs. 5 and 6, two flaps are employed, referenced 5 and 6. In this embodiment, the ring 2 has, but in non-limiting manner, an elliptic form in profile in plane. View in this application, the pivot of each flap 5, 6 is in the form of a wire 7 adapted to develop a reaction so as to return to its initial position when it undergoes a torsion. Such a wire must, in addition, be biocompatible, biostable and non-degradable, qualities which are indispensable for cardio-vascular applications. It is for example made of materials employed for non-degradable surgical sutures, such as those existing on the market: plastic, metallic, composite, carbon fibers, etc. ...

As in the above industrial application, each flap 5, 6 is fastened from rotation relative to the torsion member or wire, for example by overmoulding on a locally deformed part, to the central section 71 of the wire 7. In the cardiac application given by way of non-limiting example, there are on the ring two pairs of corresponding bores 22-23 which, in the present case, have been referenced 22 and 23 respectively opposite flap 5 and 22a, 23a opposite flap 6. Here again, that part of the wire 7 which projects beyond each flap 5, 6 freely passes through the bores, so that the latter constitute bearings for the rotation of said wire upon rocking of the flaps. The two free ends 72, 73 of each wire 7 are then applied against the outer face of the ring 2 where they are secured in a groove 24 by any means, for example by ultrasonic welding. In this way, the same result is obtained as that attained by the spring steel pivot 4 described with reference to FIGS. 1 to 4.

In order to avoid the wire bending, it may be subjected to a traction or tension before being fastened to the ring.

If a considerable length L of torsion of the wire is desired, it suffices to pass the wire in recesses 51, 52 and 61, 62 respectively made in the flaps and opening out on the periphery thereof leaving, however, a central section 71 of sufficient length to fasten the wire from rotating with respect to each flap.

It will be noted that the position of closure of the flaps may also be limited by engagement of their peripheral part 53, 63 against the inner wall of the ring 2 (FIG. 5). In the alternative, stops 21' may be used as described with respect to the embodiment of FIGS. 1-4.

The elastic wire 7 being of small diameter, the risks of turbulences and of coagulation at the level of the hinge are reduced. It is also possible to make prostheses of small dimensions for small orifices. Figs. 5 and 6 show a two-flap valvve, but it might comprise only one or more than two. Similarly, the shape of the ring 2, which has been shown as elliptic, may be circular or of any appropriate profile. The valvular heart prostheses thus described, which is intended to replace the orifices of the heart, may also be placed in an artificial vessel 8 illustrated in broken lines in FIGS. 5 and 6 in order to be used for certain by-passes between the ventricles and the large vessels or in an artificial heart by a suitable installation.

Here again, the wire 7 has a triple role:
(1) It maintains the flap or flaps in adequate position in the orifice of the ring 2.
(2) It performs the role of a hinge.
(3) Because of its elasticity, it accelerates closure of the flap or flaps by effect of torsion.

It will be noted that, depending on the position of the or each flap when the wire is fastened to the ring, after the flow of the fluid has stopped, either the closure of the flap is accelerated, or, on the contrary, the opening thereof.

By means of a suitable torsion of the wire at the moment of assembly, a pre-stress favourable to the opening or closure of the or each flap may be created.

Because of the structure according to the invention, the effects of the torsional couple may be easily mastered as desired, in order to avoid any hindrance to the flow of the fluid. There again, the closure or opening of the or each flap may be promoted as indicated hereinabove.

Admitting that the elasticity of the wire decreases on aging, this variation in mechanical condition will not present any drawback, since in that case the wire will constitute only a pivot for holding the flaps in a manner similar to those used up to the present time in practice.

In position of total opening, the flap or flaps placed in the axis of the stream of fluid do not risk remaining blocked thereby provoking an irremediable cardiac accident. The torsional force of the elastic wire being maximum in totally open position, a return device is obtained, superior to the magnetic means already used, of which the attraction decreases with the distance and is therefore especially felt when the two magnetized surfaces are very close to each other, i.e. towards the closure of the flaps.

Figure 7:
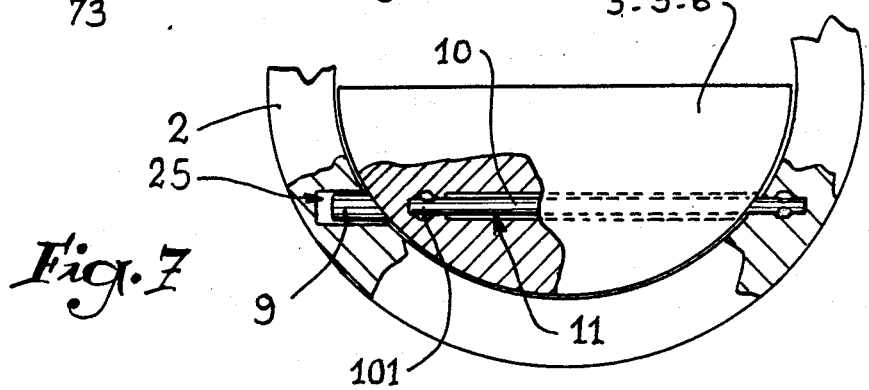
FIG. 7 shows a variant embodiment.

In the embodiment of FIG. 7, the flap 3 or each flap 5, 6 comprises a pivot 9 engaged in a hole 25 in the ring 2 and one elastic element 10 of long length disposed on the same geometrical axis. The inner end 101 of the element 10 anchored in the flap. The rest of element 10 passes through a recess 11 made in the flap is anchored to the ring as indicated hereinabove. Such a structure makes it possible to obtain a considerable restoring torque due to the length over which the angular deformation occurs.

It must, moreover, be understood that the foregoing description has been given only by way of example and that it in no way limits the domain of the invention which would not be exceeded by replacing the details of execution described by any other equivalents.

In particular, it goes without saying that the elastic elements, such as 4, may be made in two parts disposed on the same geometrical axis and of which the two ends are fixedly secured respectively to the corresponding flap and to the outside of the ring. In addition, it is obvious that, by displacing the location of pivots 7, either a central opening (FIGS. 5 and 6) may be obtained, or a lateral opening, for example by bringing the pivots closer to the centre of the ring 2.

What is claimed is:

1. A valve for a valvular heart prosthesis comprising a ring member defining an opening having a first central axis extending centrally of said opening so as to be generally perpendicular to said ring member, at least one flap for selectively closing and opening said opening through said ring member, said flap having an outer periphery which is separate from said ring member, at least one elongated torsion member pivotally mounting said at least one flap to said ring member, said torsion member having inner and outer portions and an intermediate portion therebetween, said outer portion being fixedly secured to said ring member, said inner portion being spaced inwardly of the periphery of said flap, and being fixedly secured to said flap, said flap being pivotally moveable from a first position in which said flap extends generally across said opening defined by said ring member to thereby obstruct said opening to a second position generally parallel to said first axis thereof, said torsion member having a single elongated axis along said outer portion, said intermediate portion and said inner portion and exhibiting an elastic moment of force about said elongated axis when said intermediate portion is twisted about said elongated axis as said flap is pivoted relative to said ring member, said moment of force of said intermediate portion of said torsion member thereby urging said flap to return to said first position after said flap is pivoted therefrom.

2. The valve of claim 1 wherein said at least one torsion member is torsionally prestressed when said flap is in said first position.

3. The valve of claim 1 in which said ring member includes inner and outer surface portions, at least one pair of spaced and axially aligned openings through said ring member, said intermediate portion of said torsion element extending through said pair of spaced openings, and said torsion member having a pair of spaced outer portions and a pair of spaced intermediate portions, said outer portions being secured to said outer surface of said ring member.

4. The valve of claim 3 wherein said flap includes a pair of spaced axially aligned recessed therein, said intermediate portions of said torsion member extending through said recesses.

5. The valve of claim 4 wheren said inner portion of said torsion member is disposed generally centrally with respect to said pair of spaced outer portions.

6. The valve of claim 4 includinng two of said flaps and two spaced and generally parallel torsion members, each of said torsion members pivotally mounting one of said flaps to said ring member.

7. The valve of claim 1 wherein said flap includes a pair of spaced axially aligned recesses therein, said torsion member having a pair of outer end portions and a pair of intermediate portions, said intermediate portions extending through said recesses.

8. The valve of claim 1 including two of said flaps and two spaced and generally parallel torsion members, each of said torsion members pivotally mounting one of said flaps to said ring member.

9. The valve of claim 1 in which said ring member includes stop means extending inwardly of said opening so as to be engaged by said flap when said flap is in a position to close said opening in said ring member.

10. The valve of claim 1 wherein a rigid pivot member is secured to said flap in alignment with said torsion member, said pivot member having an outer end, and including a bearing opening formed in said ring member, said pivot member being rotatably seated within said bearing opening.

11. The valve of claim 10 in which said flap includes an elongated recess therein, said intermediate portion of said torsion element extending through said recess.

* * * * *